United States Patent [19]

Mock et al.

[11] Patent Number: 5,840,312
[45] Date of Patent: Nov. 24, 1998

[54] **RECOMBINANT *BACILLUS ANTHRACIS* STRAINS UNABLE TO PRODUCE THE LETHAL FACTOR PROTEIN OR EDEMA FACTOR PROTEIN**

[75] Inventors: Michele Mock, Paris, France; Angel Cataldi, Buenos Aires, Argentina; Corinne Pezard, Paris, France

[73] Assignee: Institut Pasteur, Paris Cedex, France

[21] Appl. No.: 325,647

[22] Filed: Oct. 19, 1994

Related U.S. Application Data

[63] Continuation of Ser. No. 961,914, Mar. 2, 1993, abandoned.

[30] Foreign Application Priority Data

May 2, 1991 [FR] France ................................ 91 05417

[51] Int. Cl.$^6$ .......................... A61K 39/07; C12N 15/31; C12N 15/75; C12N 15/70
[52] U.S. Cl. ................. 424/200.1; 435/69.3; 435/320.1; 435/172.3; 435/252.31; 424/93.46; 424/235.1; 424/246.1; 536/23.7
[58] Field of Search ............................... 435/67.3, 320.1, 435/172.3, 252.31; 424/93.46, 200.1, 235.1, 246.1; 536/23.7

[56] References Cited

FOREIGN PATENT DOCUMENTS 2181435  4/1987  United Kingdom .
90/11688 10/1990 WIPO .

OTHER PUBLICATIONS

Burgess et al. The Journal of Cell Biology 111:2129–2137, Nov. 1990.
Lazar et al. Molecular and Cell Biology 8(3):1247–1252, Mar. 1988.
World Patent Index Latest, Week 9042, Derwent Publications Ltd., London, GB, AN 90–319062 {42} & SU, A, 1,551,382 (Kish Medicine Inst) Mar. 23, 1990.
Infection and Immunity, vol. 54, No. 2, 1986, Washington, D.C., US, Ivins BE. et al: "Cloning and Expression of the *Bacillus–anthracis* Protective Antigen Gene in *Bacillus–subtilis*", pp. 537–542.
Infection and Immunity, vol. 59, No. 10, 1991, Washington, D.C., US, Pezard C. et al: "Contribution of Individual Toxin Components to Virulence of *Bacillus–anthracis*", pp. 3472–3477.
Molecular Microbiology, vol. 4, No. 7, 1990, New York, US, Cataldi et al: "Construction and Characterization of a Protective Antigen–Deficient *Bacillus anthracis* strain", pp. 1111–1117.
Toxline Database, Bethesda, MD, US, Ivins BE.: "Search for a New–Generation Human Anthrax Vaccine" abstract NTIS/ AD–A190 178–4 & Govt Reports Announcements & Index, Issue 14, 1988.
Biosis Previews Database, Biosis, Philadelphia, PA, US, Singh Y. et al: "A Deleted Variant of *Bacillus anthracis* Protective Antigen is Non–Toxic and Blocks Anthrax Toxin Action in Vivo", abstract No. 89025806, & J. Biol. Chem., 264,32, 1989, 19103–7.

*Primary Examiner*—Anthony C. Caputa
*Attorney, Agent, or Firm*—Oblon, Spivak, McClelland, Maier & Neustadt, P.C.

[57] ABSTRACT

A recombinant strain of *B. anthracis* is characterized in that it can induce the production of protective antibodies against virulent strains of *B. anthracis* in a human or animal host, and characterized also by the mutation of the pX01 plasmid of at least one given gene coding for a protein which causes a toxic effect of *B. anthracis*, wherein said mutation leads to the deletion of all or part of said gene which codes for the protein causing the toxic effect, and to the insertion of a DNA cassette at said gene's deletion site in pX01, whereby the strain thereby modified may be selected and a back mutation of the recombinant strain may be prevented, and wherein the gene thereby mutated is thereafter either unable to produce the protein causing the toxic effect for which it codes, or able to code for a truncated protein which has lost its toxic properties. The use of such a strain in immunogenic compositions is also described.

36 Claims, 2 Drawing Sheets

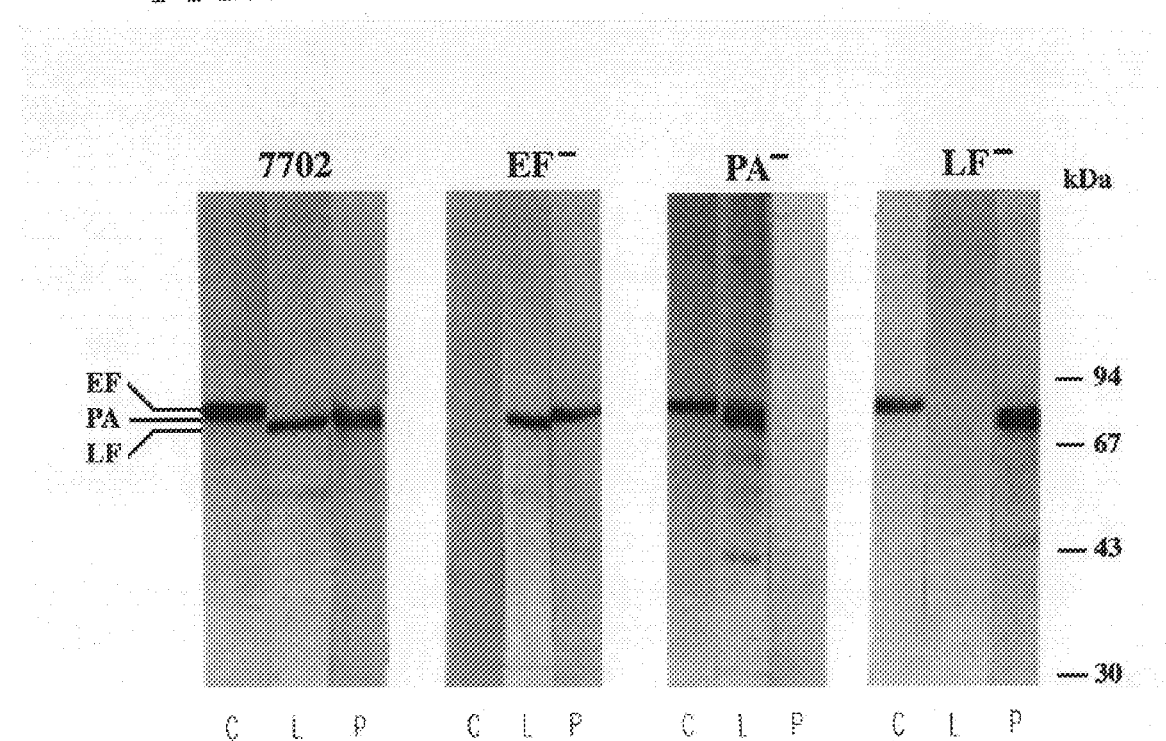

RECOMBINANT BACILLUS ANTHRACIS STRAINS UNABLE TO PRODUCE THE LETHAL FACTOR PROTEIN OR EDEMA FACTOR PROTEIN

This application is a Continuation of application Ser. No. 07/961,914, filed on Mar. 2, 1993, now abandoned.

The present application relates to non-toxicogenic and immunogenic recombinant strains of *Bacillus anthracis* and immunogenic compositions containing them.

*Bacillus anthracis* (*B. anthracis*) is responsible in man and animals for anthrax which exists in an intestinal, pulmonary and cutaneous form. The severe forms of this disease may lead to the death of the subject infected. The pathogenicity of *B. anthracis* is expressed in two ways: a toxic effect made evident by the appearance of an edema, and a so-called lethal toxic effect which may lead to the death of the subject infected. These effects are attributed to the presence in *B. anthracis* of three protein factors acting in pairwise combinations. One of the three factors is present in both combinations and is involved in the binding of the toxins of *B. anthracis* to the membrane of the host. The two other protein factors constitute the active elements responsible for the manifestation of either the toxic effect of the edema type or the toxic effect with lethal character. These two factors are called respectively edematogenic factor (English abbreviation: EF) and lethal factor (English abbreviation: LF).

The factor responsible for the membrane binding is called protective antigen (English abbreviation: PA) since, during immunization assays, the capacity to confer active protection against the disease was initially attributed to it.

The three factors PA, LF and EF have been purified (FISH et al., 1968a J. Bacteriol. 95: 907–917) and the two toxins obtained by combination of PA and LF, on the one hand, and PA and EF, on the other, have been described by LEPPLA et al. (1982, PNAS-USA 79-3162–3166).

It is also known that the three genes pag, cya and lef coding for the factors PA, EF and LF, respectively, are distributed on a plasmid pX01 of *B. anthracis* described by MIKESELL P. et al (1983 Infect. Immun. 39, 371–376).

Another plasmid pX02 has been detected in *B. anthracis*; it bears in particular the DNA sequences coding for the elements of the capsule of the bacillus.

The genes pag, cya and lef have been cloned and sequenced. The results have been reported by WELKOS et al., 1988 in Gene, 69: 287–300, by ESCUYER et al., 1988 in Gene, 71: 293–298, and by BRAGG et al., 1989 in Gene, 81: 45–54, respectively.

In addition, CATALDI et al. (Molecular Microbiology 1990 4(7), 1111–1117) have described the construction and characterization of a strain of *B. anthracis* lacking the plasmid pX02 and lacking the PA antigen by modification of the plasmid pX01.

In order to achieve this construction CATALDI et al. used a transferable, mobilizable shuttle vector by conjugation of *E. coli* with *B. anthracis*. This vector contained, on the one hand, the gene coding for the PA protein, mutated by deletion of a fragment less than 50 bp in size and, on the other, a cassette of reporter DNA bearing a gene for resistance erythromycin (Erm$^r$) inserted at the deletion site.

The vector thus formed was introduced by conjugation into *B. anthracis* 7702 (Sterne strain) and the transconjugants which had undergone homologous recombination between the vector introduced and the plasmid pX01 leading to the introduction of an inactive pag gene in pX01 in the place of the original pag gene were selected.

According to the authors of the publication, the construction achieved made it possible to show that the absence of expression of PA is sufficient to completely abolish the lethal character of *B. anthracis* and also made it possible to confirm that PA plays a central role, by enabling EF or LF to penetrate into eucaryotic cells.

According to the authors of this publication, additional studies are necessary to provide information relating to the expression of the pathogenic character of *B. anthracis* and concerning the elements likely to be involved in immunization against this bacillus.

Apparently contradictory data relating to PA were in fact available in the prior art which established, on the one hand, that PA is the principal component among the factors involved in toxicity, being required for protection against *B. anthracis* and, on the other, that a living vaccine based on spores of the Sterne strain is more effective than an acellular preparation of PA.

From this starting point the authors concluded that it was necessary to clarify the role of the components of the toxins and other antigens in order to study which might provide effective protection against virulent strains of *B. anthracis*.

According to another publication (M. MOCK, Annales de l'INSTITUT PASTEUR, Décember 1990) analyses of samples of serum taken from patients infected with *B. anthracis* made it possible to demonstrate antibodies directed against PA, EF and LF, the last factor triggering the greatest response. The conclusion of the article is that LF is a potent immunogen.

The available data relating to the pathogenicity of *B. anthracis* as well as to the elements involved in immunization have hitherto not made it possible to really define what might be a vaccinating composition providing protection against *B. anthracis*.

The results so far known have led to the consideration that such a composition could contain living strains of *B. anthracis*. However, the results described in the articles mentioned above do not enable the conditions to be defined under which these strains ought to be used in order to reap the benefit of their supposed immunogenic components (in particular, LF according to the article of MOCK) knowing that PA was recognized to play a central role among the factors responsible for toxicity, in order to trigger a protective immune response in man or animals, since these strains were, in addition, non-toxic and stable in the host.

The inventors of the present application have investigated and developed immunogenic compositions capable of inducing protective antibodies in animals. Contrary to the case of the PA recombinant strain of *B. anthracis* described in the article already mentioned by CATALDI et al., in which the mutation of the plasmid pX01 of *B. anthracis* concerned an element not directly responsible for toxicity, the inventors have put forward the hypothesis according to which a strain of *B. anthracis* lacking at least one of its toxicity factors, a factor responsible for pathogenicity and generally implicated in the reaction leading to the production of protective antibodies, might be included in the constitution of an immunogenic composition providing protection against *B. anthracis*.

In spite of the observation according to which the lethal factor LF is supposed to be a potent immunogen (MOCK, Annales de l'INSTITUT PASTEUR), the inventors have prepared and characterized in particular a recombinant strain of *B. anthracis* in which the gene coding for the LF protein is mutated in a manner such that it is no longer expressed in the bacterium or in a manner such as to be expressed in the form of an inactive truncated protein. They have observed that the mutation of the plasmid pX01 at the level of the lef gene does not impair functions other than those linked to the expression of LF in B. anthracis.

Similarly, they have shown that a mutation of the cya gene responsible for the second toxic effect could lead to the production of recombinant strains of B. anthracis which are useful for the preparation of vaccines.

Consequently, a modification of the components responsible for the toxicity of B. anthracis leading to their disappearance or their inactivation does not impair the potential of B. anthracis strains to be immunogenic and protect against infection by this bacillus.

The invention thus relates to a recombinant strain of B. anthracis, characterized by:
- its capacity to induce in a human or animal host the production of protective antibodies against virulent strains of B. anthracis,
- the mutation of at least one given gene on the plasmid pX01 coding for a protein responsible for a toxic effect in B. anthracis, this mutation resulting in:
  - the deletion of all or part of this gene coding for a protein responsible for a toxic effect and,
  - the insertion at the site of deletion of this gene in pX01 of a cassette of DNA making possible the selection of the strain thus modified and preventing the back mutation of the recombinant strain, the gene thus mutated being then either devoid of the capacity to produce the protein responsible for the toxic effect for which it codes, or capable of coding for a truncated protein lacking its toxic character.

In the framework of the invention, the term "protective antibody" designates antibodies capable of conferring protection against the virulent strains of B. anthracis, when they are produced in a human or animal host. Hence they are in particular neutralizing antibodies with respect to B. anthracis.

A protein which enters into the composition of a toxin and is necessary for the manifestation either of an edema or of lethal toxicity, even if this effect results from the combination of the activities of several factors, is called a protein responsible for a toxic effect of a B. anthracis strain. Two proteins in particular meet this definition: the protein EF and the protein LF which contribute to the formation of toxins, constituted respectively in this case by the combinations PA+EF and PA+LF.

The DNA cassette inserted into the deleted gene is a sequence of DNA which enables the integration of the deleted gene in the plasmid pX01 to be verified, since this cassette is inserted at the site of the deletion of the gene.

The deletion of at least a part of the gene coding for the protein with a toxic effect prevents the recombinant strain thus obtained from returning to its natural state by back mutation and consequently from being able to express the protein encoded in the gene or from producing it in an active form.

The mutation of the plasmid pX01 at the site of one of the genes coding for EF or LF is achieved in a particularly advantageous manner owing to the implementation of an intermediary step involving a vector itself bearing the mutated cya or lef gene which, as a result of homologous recombination, will make it possible to modify pX01 at the cya or lef gene, respectively. It is however understood that any procedure giving rise to the desired mutation of the cya gene or the lef gene may be used, whether it is direct or not.

A first family of recombinant B. anthracis strains according to the invention corresponding to the preceding definition is characterized in that in addition to the aforementioned characteristics, the strain lacks the plasmid pX02. This plasmid pX02 is necessary in particular for the formation of the capsule of B. anthracis and its absence enables the virulence of the natural strain to be attenuated.

Among the strains lacking this plasmid mention may be made of the strain Sterne 7702 described in the article by CATALDI et al. (Molec. Microbiology 1990 4(7), 1111–1117 and Sterne 1939, Onderstepoort J. Vet. Sci. Anim. Indust. 13: 313–317).

According to a first advantageous embodiment of the invention, a recombinant strain of B. anthracis is a strain in which the lef gene of the plasmid pX01, which codes for the lethal protein LF, is mutated. Such a recombinant strain expresses the toxin formed by the combination PA+EF. In this case the LF protein is no longer expressed or is expressed in the form of an inactive protein. This strain, which will be designated in the subsequent description as LF⁻ strain, has proved to be a stable strain in animals and capable of inducing protective antibodies against B. anthracis.

The inventors have observed that a deletion in the lef gene under the conditions described above does not modify the properties of the bacteria except for the absence of toxicity resulting from the modification with respect to the LF protein and is also not lethal for the bacterium.

A recombinant strain of B. anthracis particularly preferred in the context of the implementation of the invention is thus characterized in that it is capable of expressing the PA and EF proteins and in that it does not express the LF protein.

In this respect, the invention relates in particular to the LF⁻ strain (RP10) deposited on 2 May 1991 with the CNCM (Collection Nationale de Culture et de Microorganismes) Institut Pasteur, 28, rue du Dr Roux, 75724 Paris Cedex 15, France, under the number I-1095.

According to another advantageous embodiment of the invention the recombinant strains of B. anthracis are characterized in that the mutated gene of pX01 is the cya gene coding for the edematogenic protein EF.

In this case, the plasmid pX01 either does not express the EF protein or expresses it in a truncated form which is inactive with respect to its toxic character.

A preferred EF⁻strain is the strain RP9 deposited on 2 May 1991 with the CNCM under the number I-1094.

Strains are produced in particular which produce only the toxin PA+LF. Provided that the lethal character of the LF protein can be controlled, these strains may be used for the production of immunogenic compositions.

According to another embodiment of the invention, the recombinant strain of B. anthracis included in one of the groups defined above, is characterized in that the plasmid pX01 is also mutated in the gene coding for the PA protein, in a manner such that this protein either is not expressed in the recombinant strain or is not functional in the recombinant strain with respect to its role in the toxic activity of the strain as a result of binding to the cell membranes of the host.

In conformity with this embodiment, the strain formed produces only the EF protein or only the LF protein or one of these proteins accompanied by a PA protein which is inactive as far as its toxicity is concerned. Consequently, the induction of the toxic effect which results from the penetration of B. anthracis into cells through the intermediary of the PA protein cannot occur and the toxic effect due to LF or EF cannot arise.

A strain thus defined as being deficient in PA, at least in the active form, is the strain RP8 deposited with the CNCM under the number I-1093 on 2 May 1991.

Other useful strains in the context of the invention exhibit a mutation of several of the protein factors implicated in the pathogenicity of B. anthracis. In particular, these strains can be "double mutants" and in this respect mention may be made of the strains RP31 (EF+, LF−, PA−), RP4 (LF+, EF−, PA−) and RP42 (PA+, EF−, LF−).

Such strains can also thus be useful for the production of vaccines.

The cassette of DNA integrated into the plasmid pX01 of the recombinant B. anthracis strain bears, according to a first embodiment of the invention, a gene for resistance to an antibiotic and in particular a gene for resistance to kanamycin. Other types of resistance can be used, for example resistance to erythromycin.

According to another embodiment of the invention, this cassette is provided with a metabolic marker and its presence in the recombinant strain is checked by a reaction of the enzyme-substrate type.

Irrespective of its nature, the cassette makes possible the selection of strains of B. anthracis which have undergone a mutation in the pX01 plasmid.

The deleted fragment of the gene implicated in the toxic activity at the level of pX01 may be constituted by all or part of the cya gene or of the lef gene in particular. The size of the deleted fragment is advantageously greater than 0.1 kb if it is desired to completely eliminate the production of the protein naturally encoded in the gene and do so without taking into account which part of the gene is essential for the expression of this protein.

Advantageously, the deleted fragment of the cya gene or the lef gene is a fragment of at least 0.5 kb, and preferably greater than 1 kb. The deletion may relate to the promoter of the cya or lef genes but it also includes the deletion of a part of the coding sequence for the protein in order to prevent in particular any back mutation of the deleted gene.

It is understood that the recombinant strains of B. anthracis may also be characterized by a mutation of the plasmid pX01 by mutation of the two genes lef or cya, according to what is described above for each of the genes. These strains may be used in the framework of the invention for the production of protective antibodies.

In another particular embodiment of the invention, the recombinant strain of B. anthracis is also characterized in that it comprises, in addition, a heterologous nucleic acid, mutated if necessary, which codes for a defined immunogenic factor under the control of regulatory elements allowing its expression in B. anthracis.

This heterologous gene codes for a so-called immunogenic factor capable of leading to the production of antibodies in a host to which the recombinant B. anthracis is administered. Where appropriate, this immunogenic factor may benefit from the environment provided by B. anthracis in which it is expressed in order to lead to the production of neutralizing antibodies.

In other words, the heterologous factor is immunogenic as such or is constituted of a hapten rendered immunogenic by the fact of its expression within B. anthracis and/or by the fact of its association with a carrier molecule. In this case the recombinant strain of B. anthracis behaves as a vector of the immunogenicity or as a carrier strain.

In an interesting manner it will hence be possible to associate in B. anthracis the mutated nucleotide sequences of the plasmid pX01 with a heterologous nucleic acid coding for any amino acid sequence likely to be of importance in human or veterinary medicine from the point of view of vaccination.

The heterologous sequence may be transferred to B. anthracis by means of a plasmid, in particular a mobilizable and replicable shuttle plasmid.

Subsequent to its integration into B. anthracis this sequence may be maintained on this exogenous plasmid or, conversely, integrated for example in the plasmid DNA of pX01 under conditions not affecting the characteristics of the modified recombinant strain with respect to what has been said about its toxicity.

Advantageously, the recombinant strains of B. anthracis can be stored and used in the form of spores. In fact, the spores represent a useful mode of storage since they are characterized by transient latency. Once administered to the human or animal host, these spores germinate to give rise to the recombinant bacterium.

The subject of the invention is also an immunogenic composition making possible the production of neutralizing and protective antibodies towards B. anthracis in the host to which it is administered, characterized in that it contains as active ingredient a recombinant strain of B. anthracis according to the invention, as a mixture with a pharmaceutically acceptable vehicle.

As an example of such an immunogenic composition, mention may be made of that which contains as active ingredient the strain RP42 or the strain RP9.

The invention also relates to a composition of mixed vaccines characterized in that it contains as active ingredient a recombinant strain of B. anthracis of the invention under conditions such that its administration to a defined host leads to the production of protective antibodies against both an infection by B. anthracis and against the organism from which the heterologous sequence of amino acids is derived.

Such compositions may be administered by injection or by any mode of administration usually used for vaccination.

Advantageously, they may also contain an adjuvant to promote the reaction.

The administerable doses of these compositions, in particular to animals, will be determined as a function of the animal it is desired to protect. It is estimated that the administration of doses varying from 10 up to 100 times, or even more, the dose of the Sterne strain used ($10^6$ bacteria per mouse) may be considered.

Also included in the framework of the invention is a recombinant vector, in particular selected from the vectors of the shuttle type capable of infecting both Gram-negative and Gram-positive bacteria, in particular E. coli and B. anthracis, which is stable and does not integrate into the chromosome of B. anthracis and which includes at one site inessential for its replication on the one hand a mutated sequence of at least one gene coding for a protein responsible for the toxic effect of the toxins of B. anthracis, in a manner such that it does not allow the production of this protein or that this protein is produced in an inactive form with respect to the toxic effect and, on the other, a cassette of DNA capable of behaving as a reporter, for example by conferring resistance to an antibiotic, for example kanamycin, or by giving rise to a metabolic reaction towards a given substrate when this vector is introduced into B. anthracis.

A preferred recombinant vector is the vector in which the mutated gene in pX01 is the cya gene. According to another useful embodiment of the invention, this recombinant vector comprises a mutated lef gene on the plasmid pX01.

Other recombinant vectors which can be used are characterized in that the plasmid pX01 is mutated at both genes, for example at the genes LF and PA, or EF and PA or EF and LF.

Particularly useful vectors for the realization of the invention are the plasmid PMMA110 and the plasmid pCPL110.

The recombinant vector according to the invention may also contain, in addition to the sequences previously described, a heterologous DNA coding for a defined immunogenic protein.

The invention relates in addition to a procedure for the preparation of a recombinant strain of *B. anthracis* which complies with the above definitions and comprises the following steps:

the modification of defined strains of *B. anthracis* by a recombinant vector such as that described above under conditions leading to the integration of the mutated sequence of the cya gene or the mutated sequence of the lef gene as well as the reporter cassette into the plasmid pX01 and, where appropriate, the integration of the heterologous nucleic acid such that the mutated cya sequence or the mutated lef sequence is inserted by homologous recombination in pX01 at the original site of the cya gene or lef gene, respectively, the recovery of the recombinant *B. anthracis* strains, after removal of the recombinant vector not integrated into pX01.

Also included in the framework of the invention are the DNA sequences coding for a protein responsible for the toxic effect of *B. anthracis*, characterized in that they are mutated by deletion under conditions such that the protein for which they code naturally is not produced or is produced in a truncated form which is inactive as regards toxicity, in particular this relates to the coding sequences of the lef gene or of the cya gene.

The invention also relates to the plasmid pX01 mutated as has been previously defined at the lef gene or the cya gene.

BRIEF DESCRIPTION OF THE DRAWINGS

Other advantages and properties of the invention will also become apparent in the FIGS. and the examples which follow.

FIG. A–B: diagram of the mutagenesis of the cya gene (A) and of the lef gene (B)

FIG. 2: protein contained in different culture supernatants of *B. anthracis* analysed by immunoblot and verification with anti-EF (A/), anti-LF (B/) or anti-PA (C/) immunosera. 20 µg samples of 1/7702 strain of *B. anthracis*
2/EF⁻ strain of *B. anthracis*
3/PA⁻ strain of *B. anthracis*
4/LF⁻ strain of *B. anthracis*

EXAMPLES

I—Construction of Mutant Strains

MATERIALS AND METHODS

Figure 1B:
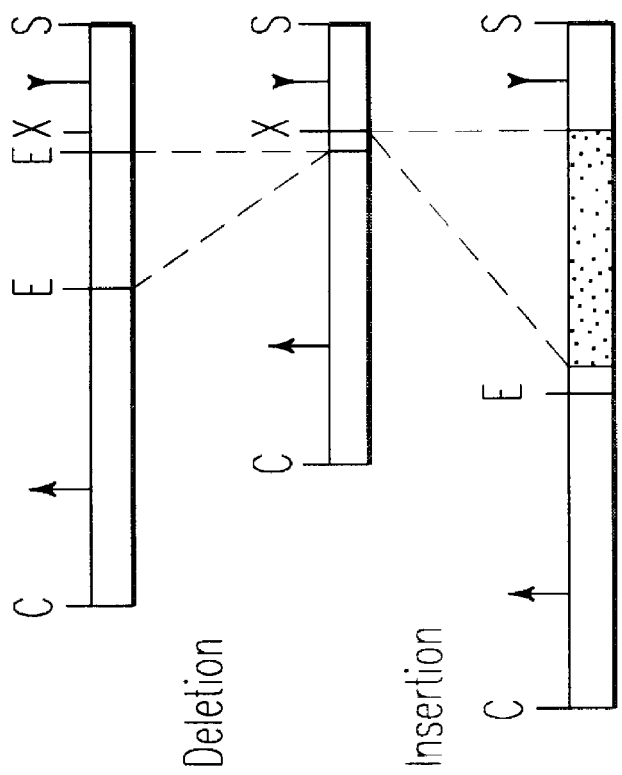
Figure 1A:
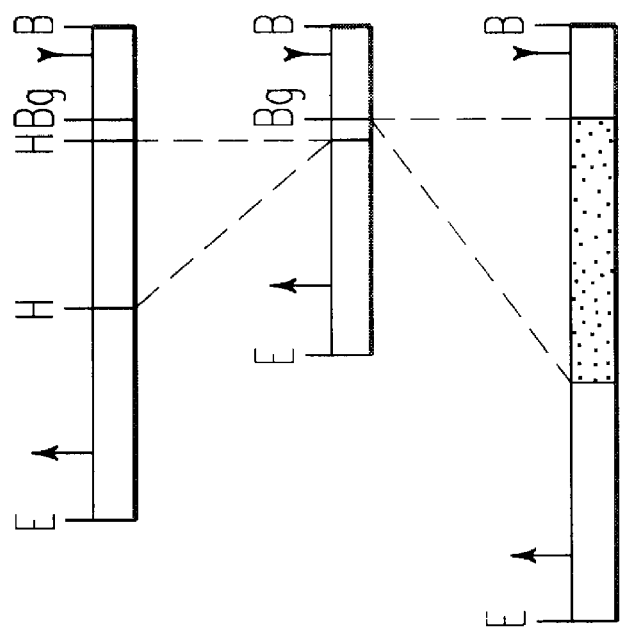

Bacterial strains, plasmids and culture media.

The bacterial strains and the plasmids used are listed in Table I. The shuttle vector between *Escherichia coli* and *Bacillus anthracis* is pAT18, used in these experiments to transform *B. anthracis*. It contains a gene for resistance to erythromycin which is capable of being expressed both in Gram-negative bacteria and Gram-positive bacteria.

L. broth or L agar media were used to grow *E. coli* (Miller 1972, Experiments in molecular genetics, Cold Spring Harbor Laboratory). *B. anthracis* was grown routinely in BHI medium (Difco laboratories) or in NBY medium for the preparation of the spores. A R medium (Ristroph and Ivins 1983, Inf. Imm. 39:483–486) was used for the production of toxins. The antibiotics were used at the following concentrations: ampicillin at 100 µg/ml in a culture of *E. coli*; kanamycin at 50 µg/ml and 20 µg/ml in cultures of *E. coli* and *B. anthracis*, respectively; erythromycin at 180 µg/ml and 10 µg/ml in cultures of *E. coli* and *B. anthracis*, respectively.

DNA procedures pX01 was prepared in conformity with the method of Green et al. 1985 (Inf. Imm. 49: 291–297). The plasmid DNA of *E. coli* and *B. anthracis* was prepared according to the method of Birnboim and Doly (Methods for recombinant DNA technology, Maniatis et al. 1982). The cassette of DNA conferring resistance to kanamycin was prepared by using the Geneclean kit (Bio 101, La Jolla, Calif.) after electrophoresis on agarose gel.

Conjugation procedures

The recombinant shuttle plasmids were transferred into *B. anthracis* 7702 (Sterne strain) by conjugation. The mating system using filters described by Trieu Cuot et al. (1987 FEMS Microbiology Letters 48, 289–294) was used in conformity with the description of Cataldi et al. *E. coli* and *B. anthracis* were grown in L and BHI media. $5 \times 10^8$ cells of *E. coli* and 108 cells of *B. anthracis* were mixed, washed to remove the antibiotics and loaded onto a 0.45 µ Millipore filter placed on BHI agar. After 15 hours of incubation at 37° C., the cells were resuspended and spread on a selective medium containing the appropriate antibiotics. The resistance of *B. anthracis* to colicins E3 and D was used to select the donors sensitive to *E. coli* by counting. The plasmid DNA was purified from the transconjugants and used to transform *E. coli*. The plasmids were tested to check for the absence of rearrangements by analysis with restriction enzymes.

Isolation of mutant strains of *B. anthracis*

The mutant strains of *B. anthracis* were obtained by culture for several generations in the absence of erythromycin but in the presence of kanamycin in order to select the recombination events between the mutated gene containing the cassette and pX01 and in order to select the strains which had lost the recombinant plasmid. Of all of the kanamycin-resistant strains tested all were sensitive to erythromycin and lacked plasmids. The characterization of the recombinants was completed by preparing the DNA of pX01 and by sub-cloning the inactivated genes in pUC18 in *E. coli*. The plasmid DNA was purified from the Kan$^r$-Amp$^r$ transformed (resistant to both kanamycin and ampicillin) and tested for the absence of rearrangements by analysis with restriction enzymes.

Adenylate cyclase assay

Adenylate cyclase was assayed in culture supernatants of *B. anthracis* in R media as described by Ladant 1988 (J. Biol. Chem. 263: 2612–2618). The enzymatic activity is expressed in unit/ml which corresponds to 1 nM/min/ml.

Protein analysis

Electrophoresis on a 8% polyacrylamide gel in the presence of SDS was carried out according to the description of Laemmli 1970. The gels were either stained with Coomassie Blue or subjected to immunoblot analysis (Towbin et al. 1979, Proc. Natl. Acad. Sci. USA 76: 4350–4354). Western blots were performed with a serum obtained from rabbits immunized either with the EF62 protein or with the LF protein of *B. anthracis* purified from the gel. The immunodetected proteins were visualized by using protein A labelled with $^{125}$I and by autoradiography with X-ray films.

Preparation of the spores

For the preparation of spores of *B. anthracis*, a colony is streaked on a NBY medium on a sloping bed of gelose and incubated for 7 days at 30° C. The formation of the spores was checked by microscopic examination. 5 ml of sterile distilled water were added to each tube. The suspension of spores was transferred to a sterile tube and incubated in water at 65° C. for 30 minutes to kill all of the bacilli existing in this culture. The culture containing at least 90% of spores and $10^8$ CFU/ml was collected by centrifugation and suspended in water (1/20 v/v of the initial culture). The dilutions of the collection of spores were spread on a BHI agar medium for the counting of viable spores. The collection of the spores was divided into 5 ml aliquots and stored at 4° C.

Before each infection experience, the aliquots were diluted with physiological saline and the dilutions were spread on a dish of BHI agar for the determination of the viability by counting.

The spores of B. subtilis were prepared in the same way.

Infection of mice

Pathogen-free, 3 to 6 weeks old female Swiss mice were supplied by the Saint Aubin laboratory, Les Elboeuf, France. The animals were fed on sterilized water supplemented with vitamins (pH 3). The mortality was monitored by inoculating groups of 10 mice subcutaneously (sc) with suitable dilutions of suspensions of spores (in a volume of 0.2 ml) obtained from the parental strain or from the mutants. The virulence was estimated by determining the 50% lethal dose (LD 50) in groups of 3 to 10 weeks old mice by the statistical method. The survival of the bacteria was monitored in the tissues of the host by infecting the mice in the right hind paw (in a volume of 0.1 ml) with high doses of suspensions of spores derived from the strains tested. Groups of 5 mice were sacrificed at defined intervals and their hind paws were sectioned, washed with sodium hypochlorite solutions (1 min) to kill the contaminants of the skin and with sterile PBS, pH 7.2 (1 min). Then volumes of 0.1 ml of the serial dilutions (10 fold) were spread on a gelose mixture containing trypticase. The colonies were counted after 16 hours of incubation at 37° C. and the results were expressed in terms of log 10 of the bacterial counts per hind paw. At the same time the inflammatory reaction induced in the hind paw of the infected mice was measured at defined intervals using sliding calipers (Schelltaster, Hessen).

RESULTS

Construction of the mutant strains of B. anthracis deficient in EF toxin or LF toxin The genes coding for the LF protein (lef gene) or for the EF protein (cya gene) were inactivated in accordance with the procedure of Cataldi both by deletion and by insertion of a cassette resistant to kanamycin. The construction initially generated in E. coli was transferred by conjugation to the Sterne 7702 strain of B. anthracis. The cloned and sequenced cya gene (Mock et al. 1988, Gene 64: 277–284) was subcloned in E. coli in the plasmid pUC8 (pMM861).

The recombinant plasmid pMM861 (Labruyère et al. 1990 Biochemistry 29:4922–4928), which codes for the cya locus was subjected to partial enzymatic digestion at the HindIII site so as to create a HindIII deletion fragment of 1 kb within the cya gene. The plasmid was then cut at its unique BglII site in the gene and the cassette of DNA of 1 kb conferring resistance to kanamycin was ligated to the plasmid. The resulting recombinant plasmid pMMA862 was characterized starting from E. coli transformants $Amp^r$, $Kan^r$. The profiles of the plasmid preparation pMMA862 obtained with the restriction enzymes showed that the cya gene had been mutated in the desired manner. Then a 4.2 kb EcoRI-BamHI fragment of the plasmid pMMA862 was inserted into the mobilizable shuttle plasmid pAT18 ($Erm^r$) (pMMA110).

The mutagenesis of the lef gene was carried out in a similar manner. The lef gene is contained in a SacI-ClaI fragment of 3.5 kb of the plasmid pX01 of B. anthracis. This fragment was first cloned in pUC18 and made possible the expression of the lef gene in E. coli cells carrying the corresponding plasmid pCPL11. The fragment of 3.5 kb was then inserted into pAT18 (pCPL100). The recombinant plasmid pCPL100 was subjected to partial enzymatic digestion with EcoRI so as to create a 0.8 Kb EcoRI deletion fragment within the gene. The resultant plasmid was cut at its unique XhoI site within lef and the $Kan^r$ cassette was ligated to the plasmid. The corresponding recombinant plasmid pCPL110 was characterized starting from the E. coli transformants, $Erm^r$, $Kan^r$. The restriction enzyme profile of pCPL110 showed that the lef gene had been mutated in the desired manner.

The inactivated genes were then transferred into B. anthracis 7702: pMMA110 and pCPL110 bearing the mutated cya and lef genes, respectively, enabled E. coli HB101 bearing pRK212.1 to be transformed for mobilization. The strategey of transformation by the vector developed by Trieu Cuot was used between E. coli and the B. anthracis strain 7702 of Sterne so as to transfer the DNA constructions made in E. coli to B. anthracis by conjugation.

Although the transfer frequences were low ($10^{-8}$) $Erm^r$, $Kan^r$ B. anthracis transconjugants were obtained. The homologous recombination events between pMMA110 or pCPL110 and pX01 were then selected in order to verify that the inactive cya gene or the inactive lef gene had been introduced into pX01. For that purpose, the transconjugants were grown for several generations without erythromycin (Erm) (selective antibiotic for the shuttle plasmid) but in the presence of kanamycin (Kan) (selective for the cassette). All of the clones tested in conformity with this procedure were sensitive to Erm and resistant to Kan, showing the loss of pMMA110 or of pCPL110 and the integration of the $Kan^r$ cassette in pX01. The presumably recombinant B. anthracis strains $EF^-$ or $LF^-$ bearing $pX01-cya^-$ or $pX01-lef^-$, respectively, were first characterized by means of the technique described in the section Materials and Methods by analysis using restriction enzymes, then by the adenylate cyclase assay and immunoblot experiments.

Production of the toxins PA, LF and EF in the culture supernatants of the mutant strains of B. anthracis.

The adenylate cyclase activity of the EF component was determined in different strains of B. anthracis (Table 2). No activity was detected in the culture supernatants of the mutant strain $EF^-$, thus confirming the inactivation of the cya gene in pX01. In the culture supernatant of the mutant strain $LF^-$, the adenylate cyclase activity was the same (200 U/ml) as the activity usually found in the culture supernatants of the strains 7702.

The B. anthracis mutant strains were then characterized by immunoblot analysis by using a serum directed against PA, EF or LF. The sera were obtained according to the procedure described in Materials and Methods. As is shown in FIG. 2, the three proteins forming the two toxins of B. anthracis, PA, EF and LF are produced in B. anthracis 7702 when the bacteria are grown in a R medium under defined conditions. A component related to LF was not produced by the $LF^-$ mutant strains whereas PA and EF were produced. Furthermore, a component related to EF was not detected in the supernatants of the $EF^-$ mutant strains confirming the absence of adenylate cyclase activity in the culture supernatants of the $EF^-$ mutants (Table 2). In the culture supernatants of the $PA^-$ mutants, a component related to PA was not detected whereas LF and EF were still produced.

Virulence of the different strains of B. anthracis in mice

Groups of 10 Swiss mice were inoculated sc with increasing doses of different strains of B. anthracis and the mortality was monitored for 15 days. The strain 7700 corresponding to the Sterne strain 7702 lacking the plasmid pX01 which codes for the toxins, was totally avirulent (LD 50 $10^9$), as are the PA⁻ mutant strains obtained by Cataldi. The inactivation of EF significantly modified the LD 50 by 1.0 log unit (LD 50 $10^7$ spores per mouse as against 10 spores per mouse for the Sterne strain 7702). This indicates that the expression of virulence was partially affected by the absence of the adenylate cyclase. On the other hand, the lethality was totally abolished in the absence of the lethal factor since the LF⁻ mutant strains of B. anthracis were avirulent (LD 50 $10^9$). The totally avirulent LF⁻ mutant strain but which nonetheless produces the toxin for edema (PA+EF) was able to induce edema of the skin after subcutaneous injections, whereas the PA⁻ or EF⁻ mutant strains did not induce edema. It was important to verify this property in vivo and for this purpose, mice were inoculated in the right hind paw with different strains of B. anthracis ($10^8$, $10^9$ or $10^6$ spores per mouse). The intensity of the edema in the hind paw was measured with sliding calipers. The results obtained are presented in FIG. 2. The LF⁻ mutant strain was capable of inducing edema of the skin just like the Sterne 7702 strain. On the other hand, the PA⁻ or EF⁻ mutant strains of B. anthracis 7700 did not induce edema of the skin. In the case of all of the B. anthracis strains, the inflammatory reaction is exacerbated 2 days after the injection (the mice die in this experiment, the LD 50 sc in the hind paw was higher than $10^8$). When the mice were inoculated with $10^8$ spores of the Sterne 7702 strain an edema was observed for 6 days, whereas with the LF⁻ mutant strain the edema was visible for only 2 days. With the B. subtilis strain MSY no inflammatory reaction was observed ($10^6$, $10^7$ or $10^8$ spores in suspension). Finally, in order to verify whether the induction of the edema was dependent on bacterial survival in the hind paw of the infected mice, a bacterial culture was monitored when the mice were inoculated with $10^8$ spores of all of the B. anthracis strains tested.

For all of the B. anthracis strains, the log 10 of the bacterial count per paw decreased rapidly 24 hours after the injection by more than 1.0 log unit and remained stable for 10 days. This indicated that the induction of the edema was not correlated with bacterial survival at the sites of the inoculation. When the mice were inoculated with a suspension of $10^8$ spores of B. subtilis, the log 10 of the bacterial count decreased significantly. The spores were destroyed 5 days after the infection. These data demonstrated that the strain of B. anthracis (even the strain 7700) survived for a longer time than the B. subtilis strain in the tissues of the host.

TABLE 1

Bacterial strains and plasmids used.

| Strains | Plasmids | Characteristics |
|---|---|---|
| Bacterial strains | | |
| B. anthracis 7702 | pX01 | PA⁺EF⁺LF⁺ |
| B. anthracis 7700 | — | Nal$^r$ |
| B. anthracis RP8 PA⁻ | pX01-pag 322 | PA⁻EF⁺LF⁺ Erm$^r$ |
| B. anthracis RP9 EF⁻ | pX01-cya 303 | PA⁺EF⁺LF⁻ Kan$^r$ |
| B. anthracis RP10 LF⁻ | pX01-lef 238 | PA⁺EF⁺LF⁻ Kan$^r$ |
| E. coli HB101 | pRK212.1 | Amp$^r$ |
| E. coli JM105 | | |
| B. Subtilis SMY | | |
| Plasmids | | |
| pAT18: | shuttle plasmid pX01, Erm$^r$ (Trieu Cuot et al., 1987) | |

TABLE 1-continued

Bacterial strains and plasmids used.

| Strains | Plasmids | Characteristics |
|---|---|---|
| pCPL100: | | recombinant plasmid pAT18 bearing the 3.5 kb ClaI-SacI fragment of pX01 coding for LF. Erm$^r$ |
| pCPL110: | | derivative of pCPL100 bearing a Kan$^r$ cassette of 1.5 kb inserted in the LF structural gene from which a EcoRI fragment of 0.8 kb has been deleted. Kan$^r$. Erm$^r$ |
| pMMA861: | | recombinant plasmid pUC8 bearing the 3.17 kb EcoRI-BamHI fragment of pX01 coding for EF (Mock 1987). Amp$^r$ |
| pMMA862: | | derivative of pMMA861 bearing the Kan$^r$ cassette of 1.5 kb inserted into the EF structural gene from which the HindIII fragment has been deleted. Amp$^r$. Kan$^r$ |
| pMM110: | | DNA insert of 3.57 kb of pMMA861 cloned in pAT18 Erm$^r$, Kan$^r$ |
| B. anthracis 7702: | | Sterne strain 1939 J. Vet. Sci. Anim. Indust. 13: 313–317 |
| B. anthracis 7700: | | strain derived from 7702 lacking pX01 |
| B. anthracis RP8: | | strain derived from 7702 |
| E. coli HB101: | | Trieu Cuot et al., 1987 FEMS Microbiol Letters 48: 289–294 |
| E. coli JM105: | | Yannish-Perron et al., 1985 Gene 33: 103–109 |

TABLE 2

Adenylate cyclase activity in the different culture supernatants of B. anthracis

| Strains | Adenylate cyclase activity nmol/min/ml supernatant |
|---|---|
| Mutant EF⁻ | 0 |
| Mutant PA⁻ | 300 |
| Mutant LF⁻ | 200 |
| Sterne strain 7702 | 200 |

Construction of doubly mutated strains of B. anthracis

These strains were constructed according to the procedures described in the foregoing pages. They produce one of the components PA, EF or LF.

Methods

The designations of the strains and their characteristics are the following:

RP31: EF⁺ LF⁻ PA⁻ The lef gene is inactivated by insertion of the cassette for resistance to kanamycin (Kan$^R$) The pag gene is inactivated by insertion of the cassette for resistance to erythromycin (Erm$^R$).

RPA4: LF⁺ EF⁻ PA⁻ The pag gene is inactivated by insertion of the cassette for Erm$^R$ resistance. The cya gene is inactivated by insertion of the cassette for Kan$^R$ resistance.

RP42: PA⁺ EF⁻ LF⁻ The cya gene is inactivated by insertion of the cassette for Erm$^R$ resistance. The lef gene is inactivated by insertion of the cassette for Kan$^R$ resistance.

The three strains were characterized biochemically by analysis of the proteins contained in their culture supernatants (according to the method of Western Blot).

II—Immunoprotection Experiments

Experiments were undertaken in the mouse for the purpose of studying the immunoprotective potency of the mutant strains. The animals received subcutaneously spores of RP42 (PA⁺, EF⁻, LF⁻) and RP9 (PA⁺, EF⁺, LF⁻); a control group of animals received nothing.

40 days later the challenge was effected by subcutaneous injection of a lethal dose (1.5×10⁹ spores) of the Sterne strain.

The percentage of surviving animals was determined: 90% and 85% of the animals, respectively, which had received RP42 and RP9 survived the injection of the lethal dose of the Sterne strain whereas no protection whatever was observed in the control group.

The initial results are significant and indicate that the strains constructed are capable of inducing an active immunoprotection in the mouse.

We claim:

1. A recombinant strain of *Bacillus anthracis* which induces in a human or animal host the production of protective antibodies against a virulent strain of *Bacillus anthracis*, wherein said recombinant strain contains a plasmid having a mutation of a least one given gene coding for a protein responsible for a toxic effect of *Bacillus anthracis*, wherein said gene is the lef gene or the cya gene of *Bacillus anthracis*, said mutation having a deletion of at least 0.1 kb of said gene, and the gene thus mutated having the inability to produce the protein responsible for said toxic effect.

2. A recombinant vector, which is stable and non-integrative into the chromosome of *Bacillus anthracis* and which comprises at a site inessential for replication of said vector a mutated sequence comprising a deletion of at least 0.1 kb in at least one gene coding for a protein responsible for the toxic effect of a toxin of *Bacillus anthracis*, wherein said gene is the lef gene or the cya gene of *Bacillus anthracis*, such that said mutated sequence does not allow the production of said protein, and (b) a DNA cassette containing a selection marker.

3. The recombinant strain of *Bacillus anthracis*, according to claim 109, wherein said plasmid further comprises, at the site of deletion of said gene in the plasmid, a DNA cassette making possible the selection of the recombinant strains and preventing the back mutation of the recombinant strain.

4. The recombinant strain of *Bacillus anthracis* according to claim 3, which lacks plasmid pX02.

5. The recombinant strain of *Bacillus anthracis* according to claim 3, wherein said gene coding for a protein responsible for a toxic effect is the lef gene coding for the lethal protein Lethal Factor.

6. The recombinant strain of *Bacillus anthracis* according to claim 3, wherein said gene coding for a protein responsible for a toxic effect is the cya gene coding for the edematogenic protein Edema Factor.

7. The recombinant strain of *Bacillus anthracis* according to claim 3, wherein said strain is capable of expressing Protective Antigen and Edema Factor, and said strains does not express protein Lethal Factor.

8. The recombinant strain of *Bacillus anthracis* according to claim 3, wherein the plasmid is plasmid pX01 which comprises the lef gene, the pag gene and the cya gene of *Bacillus anthracis*, and plasmid pX01 is further mutated at the pag gene coding for the Protective Antigen protein, such that the Protective Antigen protein is not expressed in said recombinant strain.

9. The recombinant strain of *Bacillus anthracis* according to claim 4, wherein the plasmid is plasmid pX01 which comprises the lef gene, the pag gene and the cya gene of *Bacillus anthracis*, and plasmid pX01 is further mutated at two distinct genes, wherein the genes are selected from the group consisting of the pag gene, the lef gene, and the cya gene.

10. The recombinant strain of *Bacillus anthracis* according to claim 3, wherein said DNA cassette comprises a gene for resistance to an antibiotic or a metabolic marker.

11. The recombinant strain of *Bacillus anthracis* according to claim 3, wherein said plasmid is pX01.

12. The recombinant strain of *Bacillus anthracis* according to claim 3, wherein said plasmid further comprising a heterologous nucleic acid coding for a factor which is immunogenic, and under the control of regulatory elements for expression of said factor in *Bacillus anthracis*.

13. The recombinant strain of *Bacillus anthracis* according to claim 3, wherein the plasmid is plasmid pX01, and plasmid pX01 further comprises a heterologous nucleic acid coding for a factor which is immunogenic, and under the control of regulatory elements for the expression of said factor in *Bacillus anthracis*.

14. The recombinant strain of *Bacillus anthracis* according to claim 3, which is in the form of spores.

15. A recombinant strain of *Bacillus anthracis*, which is the strain RP9 deposited on 2 May 1991 with the CNCM under the number I-1094.

16. A recombinant strain of *Bacillus anthracis*, which is the strain RP10 deposited on 2 May 1991 with the CNCM under the number I-1095.

17. An immunogenic composition for the production of neutralizing and protective antibodies against *Bacillus anthracis* in a host to which the composition is administered, said composition comprising the recombinant strain of *Bacillus anthracis* according to claim 3, and a pharmaceutically acceptable carrier.

18. The immunogenic composition according to claim 17, comprising a recombinant strain of *Bacillus anthracis*, which is strain RP9 deposited on 2 May 1991 with the CNCM under the number I-1094.

19. The immunogenic composition according to claim 17, further comprising an adjuvant.

20. The immunogenic composition according to claim 17, comprising a recombinant strain of *Bacillus anthracis*, which is strain RP10deposited on 2 May 1991 with the CNCM under the number I-1095.

21. A vaccine comprising a recombinant strain of *Bacillus anthracis* according to any one of claims 11 to 16 and a pharmaceutically acceptable carrier.

22. A vaccine according to claim 21 further comprising an adjuvant.

23. The recombinant vector according to claim 2, which is a shuttle vector which infects Gram-negative bacteria.

24. The recombinant vector according to claim 2, which is a shuttle vector which infects Gram-positive bacteria.

25. The recombinant vector according to claim 2, which is a shuttle vector which infects *Escherichia coli*.

26. The recombinant vector according to claim 2, which is a shuttle vector which infects *Bacillus anthracis*.

27. The recombinant vector according to claim 2, wherein said vector is plasmid pX01 which further contains the deletion of at least 0.1 kb in the lef gene.

28. The recombinant vector according to claim 2, wherein said vector is plasmid pX01 which further contains the deletion of at least 0.1 kb in the cya gene.

29. The recombinant vector according to claim 2, wherein said vector is plasmid pX01 which further contains the deletion in each of two genes, wherein the genes are selected from the group consisting of the lef gene, the pag gene and the cya gene.

30. The recombinant vector according to claim 2, further comprising a heterologous DNA coding for an immunogenic protein.

31. A DNA fragment consisting of a nucleic acid sequence coding for an Edema Factor protein or a Lethal Factor protein responsible for a toxic effect of *Bacillus anthracis*, wherein said DNA fragment is mutated by deletion of at least 0.1 kb of said nucleic acid sequence, such that the DNA fragment which is mutated does not express said protein responsible for said toxic effect.

32. The DNA fragment of claim 31, wherein said nucleic acid sequence codes for the Lethal Factor protein.

33. The DNA fragment of claim 31, wherein said nucleic acid sequence codes for the Edema Factor protein.

34. A method for the preparation of a recombinant strain of *Bacillus anthracis* comprising the following steps:

a) transfecting a strain of *Bacillus anthracis* with the recombinant vector according to claim 2 that further comprises a reporter cassette under conditions for homologous recombination of said mutated sequence into plasmid pX01; and b) selecting for the recombinant strain of *Bacillus anthracis* expressing the reporter cassette.

35. The method of claim 34, wherein said gene is the cya gene.

36. The method of claim 34, wherein said gene is the lef gene.

* * * * *